United States Patent [19]

Tarr

[11] Patent Number: 4,755,185
[45] Date of Patent: Jul. 5, 1988

[54] PROSTHETIC JOINT

[75] Inventor: Richard R. Tarr, Warsaw, Ind.

[73] Assignee: Boehringer Mannheim Corporation, Indianapolis, Ind.

[21] Appl. No.: 7,331

[22] Filed: Jan. 27, 1987

[51] Int. Cl.⁴ .......................... A61F 2/30; A61F 2/40; A61F 2/38; A61F 2/42

[52] U.S. Cl. ...................................... 623/18; 623/19; 623/20; 623/21

[58] Field of Search ..................................... 623/18-21

[56] References Cited

U.S. PATENT DOCUMENTS

| | | | |
|---|---|---|---|
| 3,869,729 | 3/1975 | Attenborough | 623/20 |
| 4,085,466 | 4/1978 | Goodfellow et al. | 623/20 |
| 4,216,549 | 8/1980 | Hillberry et al. | 623/20 |
| 4,309,778 | 1/1982 | Buechel et al. | 623/20 |
| 4,470,158 | 9/1984 | Pappas et al. | 623/20 |

Primary Examiner—Ronald L. Frinks
Attorney, Agent, or Firm—Max J. Kenemore

[57] ABSTRACT

A three-component prosthetic joint comprising a first bone-attachable component having a planar articular surface and a second bone-attachable component having an arcuate articular surface and a substantially congruent bearing component held therebetween, avoids extrusion of the bearing component without reduction in the efficacy of the prosthesis as an implantable joint when the substantially congruent planar articular surfaces of the bearing component and the first component are in free-floating contact and the substantially congruent arcuate articular surfaces of the second component and the bearing component are unicentric and include a system of interlockable flanged grooves which prevent both separation of the arcuate surfaces when interlocked and also medial-lateral movement therebetween.

3 Claims, 1 Drawing Sheet

U.S. Patent    Jul. 5, 1988    4,755,185
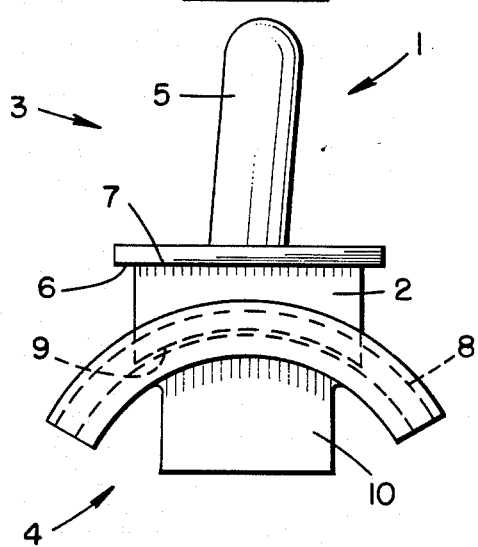
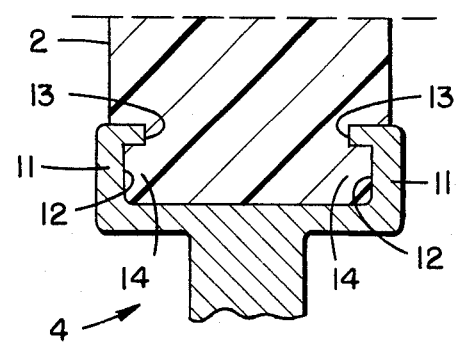
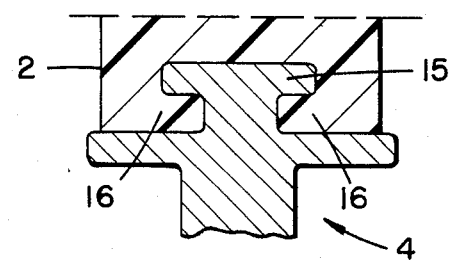
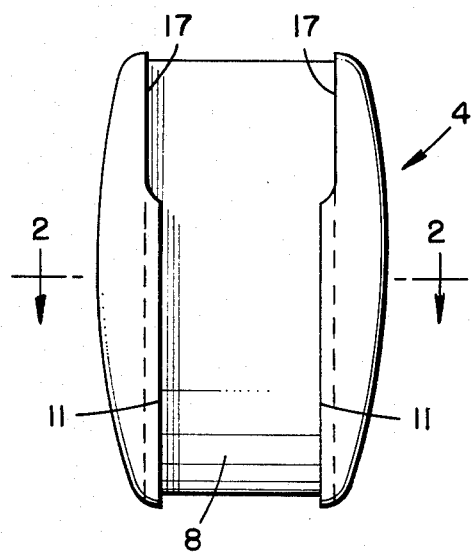
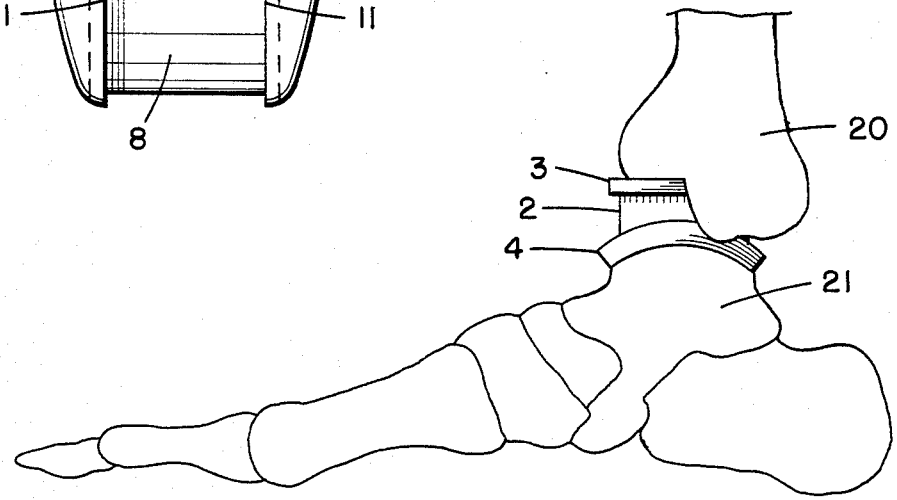

PROSTHETIC JOINT

FIELD OF THE INVENTION

The present invention relates generally to the field of implantable prostheses and, more specifically, to prosthetic joints.

BACKGROUND

The use of implantable prosthetic joints to replace natural joints in humans and in animals is an established theraputic procedure. Many designs for such prosthetic joints are known.

One example of an implantable prosthetic joint design is found in U.S. Pat. No. 4,470,158, issued Sept. 11, 1984, to Pappas et al. The prosthetic joint of Pappas et al includes a first component for attachment to a first bone, a second component for attachment to a second bone and a bearing component therebetween. There is substantially congruent engagement between the components.

Pappas et al discloses an articular surface on the second component and a corresponding congruent articular surface on the bearing component which surfaces are generated by rotating a common generating curve around a plurality of predetermined generating axes to create multicentric surfaces. The purpose of the multicentric congruent surfaces of Pappas et al is to provide a free floating or unconstrained relative motion between the bearing surface and the second component surface while discouraging extrusion of the bearing component.

Another example of a prosthetic joint can be found in U.S. Pat. No. 4,085,466, issued Apr. 25, 1978, to Goodfellow et al.

Prosthetic joints such as those identified in the above mentioned patents have enjoyed commercial success. However, in prosthetic joint designs which provide free floating contact between the bearing component and both other components, extrusion of the bearing has remained a problem in patients having weark or damaged ligaments which are not strong enough to hold the bearing component in place between the other components. There has existed a need for a prosthetic joint which provides at least some free floating contact between the bearing component and a component to be attached to a bone while at the same time capturing the bearing component so that extrusion of the bearing component is avoided.

SUMMARY OF THE INVENTION

It is an object of the present invention to provide an implantable prosthetic joint which avoids extrusion of a bearing component.

This and other objects are accomplished by the present invention which relates to a prosthetic joint comprising:
(a) a first component adapted for fixation to a first bone and having a planar articular surface;
(b) a second component adapted for fixation to a second bone and having a unicentric arcuate articular surface; and
(c) a bearing component having a planar articular surface in unconstrained substantially congruent contact with the planar articular surface of the first component and having a unicentric arcuate articular surface in substantially congruent contact with the unicentric arcuate articular surface of the second component; wherein at least a portion of the arcuate substantially congruent articular surfaces of (b) and (c) include a system of interlockable flanged grooves which, when interlocked, prevent both separation of the arcuate substantially congruent articular surfaces of (b) and (c) and medial-lateral relative movement therebetween without hindering arcuate relative movement therebetween.

In one embodiment the system of interlockable flanged grooves comprises inwardly opening U-shaped flanges along the edges of the unicentric arcuate articular surface of (b) and substantially congruent mating grooves in the unicentric arcuate articular surface of (c).

In a preferrerd embodiment the U-shaped flanges of (b) include an open portion on both edges of the arcuate articular surface of (b) which open portion enables the arcuate articular surface of (c) to be mated with the arcuate articular surface of (b) prior to arcuate relative movement therebetween which movement engages the system of interlockable flanged grooves.

BRIEF DESCRIPTION OF THE DRAWINGS

FIG. 1 shows schematically a side view of the present invention.

FIG. 2 shows a preferred arrangement of interlocking flanged groves in schematic cross-section.

FIG. 3 shows another useful embodiment of the present invention in cross-section.

FIG. 4 shows schematically a preferred flange design on the second component.

FIG. 5 shows schematically the placement of the present invention when used as an ankle prosthesis.

DETAILED DESCRIPTION

This invention is based on the surprising discovery that, in a three-component prosthetic joint comprising a first bone-attachable component having a planar articular surface and a second bone-attachable component having an arcuate articular surface and a substantially congruent bearing component held therebetween, extrusion of the bearing component can be avoided without reduction in the efficacy of the prosthesis as an implantable joint when the substantially congruent planar articular surfaces of the bearing component and the first component are in free-floating contact and the substantially congruent arcuate articular surfaces of the second component and the bearing component are unicentric and include a system of interlockable flanged grooves which prevent separation of the arcuate surfaces when interlocked and also medial-lateral movement therebetween.

FIG. 1 shows prosthetic joint 1 according to the present invention. In joint 1, bearing component 2 is held between a bone attachable first component 3 and bone attachable second component 4. First component 3 includes stem 5 for use in fixing first component 3 to a bone. First component 3 also includes planar articular surface 6 for substantially congruent contact with planar articular surface 7 of bearing component 2.

Second component 4 has a unicentric arcuate articular surface described by dotted line 8 which is substantially congruent with unicentric arcuate articular surface 9 of bearing component 2. Second component 4 also has fixation fin 10 for attachment of second component 4 to a bone.

As is shown more clearly in the cross-sectional illustration of FIG. 2, second component 4 and bearing component 2 are shaped so as to form a system of interlocking flanged groves. Opposing U-shaped flanges 11 along the edges of second component 4 and the grooves 12 formed in second component 4 by flanges 11 are substantially congruent with groves and flanges 14 in bearing component 2.

The system of interlocking flanges does not interfere with relative arcuate movement between bearing component 2 and second component 4. However bearing component 2 is captured or prevented from separating from substantially congruent contact with bearing 4 and is prevented from medial-lateral movement.

In practical use a prosthetic joint of the structure shown in FIGS. 1 and 2, the preferred embodiment, has been demonstrated to avoid extrusion of bearing component 2 when implanted as an ankle prosthesis in a patient with weak ligaments. The patient had experienced extrusion of a bearing component after a prior art ankle joint was implanted. The extrusion was due to ligament failure. The prosthetic joint of the present invention avoided extrusion of bearing component 2 even after failure of a synthetic ligament which replaced the failed ligament.

The embodiment of FIG. 2 is preferred because the outboard placement of the U-shaped flanges provides strong resistance to separation of the bearing component and the arcuate articular component. Although the embodiment of FIG. 2 is preferred, the embodiment of FIG. 3 is an example of other useful systems of interlocking flanges.

T-shaped portion 15 of bearing component 4 in FIG. 3 provides grooves which are filled with interlocking flange portions 16 of bearing component 2. The interlocking system of flanges and grooves of the embodiment of FIG. 3 capture bearing component 2 in substantially congruent contact with second bearing component 2 while avoiding medial-lateral relative movement between the components.

FIG. 4 shows a top view of second component 4. Arcuate articular surface 8 has opposing U-shaped flanges 11 which form grooves for substantially congruent cooperation with a bearing component as is shown in cross-section in FIG. 2.

In the preferred embodiment of FIG. 4, flanges 11 are cut away at opposing portions 17 of bearing surface 8. The cut away portions enable bearing component 2 to be positioned onto surface 8 before being rotated into interlocking contact with the groove defined by flange 11. It has been found that engagement of the interlocking system of grooves and flanges of bearing components 2 and 4 is facilitated by cut away portion 17. In the absence of cut away portion 17, bearing component 2 must be engaged at one end of component 4 and rotated into operative position. Although possible, such a procedure is difficult in the confines of a human joint during surgery where useable space is minimized by ligaments which keep bones on either side of the joint in contact during placement of the prosthesis.

When the preferred embodiment of FIG. 4 is used, cut way portions 17 of flange 11 are positioned so as not to be located at a position along surface 8 where bearing component 2 will operate after implantation of the prosthetic joint.

In use, the components of the prosthetic joint of the present invention may be made of any suitable material. Good results have been experienced when bearing component 2 is made from high molecular weight polyethylene and when components 3 and 4 are formed from a cobalt, chrome, molybdenum alloy. It will be readily understood by those of ordinary skill in the art of making prosthetic implants that other materials will be useful for all three components. Such other materials are intended to be within the scope of the appended claims.

The size of the prosthetic joint and its components may be varied depending, for example, on whether an ankle, wrist or shoulder or other joint is being replaced.

FIG. 5 shows the prosthetic joint of the present invention used as an ankle joint. First component 3 is attached to tibia 20 and second component 4 is attached to talus 21. Attachment is accomplished by already well known surgical methods in which the ankle joint to be replaced is removed and components 3 and 4 are fixed into the tibia and the talus by means of stem 5 and fin 10 respectively.

Bearing component 2 is positioned between component 3 and component 4. As is described above in connection with FIGS. 1, 2 and 3, the planar articular surface of bearing component 2 is in free-floating contact with planar articular surface of component 3. Arcuate articular surface of bearing component 2 is held in substantially congruent contact with component 4 by an interlocking system of groves and flanges as is shown in FIGS. 2 and 3.

The present invention has been disclosed in the above teachings and drawings with sufficient clarity and conciseness to enable one skilled in the art to make and use the invention, to know the best mode for carrying out the invention and to distinguish it from other inventions and from what is old. Many variations and obvious adaptations of the invention will readily come to mind, and these are intended to be contained within the scope of the invention as claimed below.

What is claimed is:

1. A prosthetic joint comprising:
   (a) a first component adapted for fixation to a first bone and having a planar articular surface;
   (b) a second component adapted for fixation to a second bone and having a unicentric arcuate articular surface; and
   (c) a bearing component having a planar articular surface in unconstrained substantially congruent contact with the planar articular surface of the first component and having a unicentric arcuate articular surface in substantially congruent contact with the unicentric arcuate articular surface of the second component;
   wherein at least a portion of the arcuate substantially congruent articular surfaces of (b) and (c) include a system of interlockable flanged grooves which, when interlocked, prevent both separation of the arcuate substantially congruent articular surfaces of (b) and (c) and medial-lateral relative movement therebetween without hindering arcuate relative movement therebetween.

2. The prosthetic joint of claim 1 wherein the system of interlockable flanged grooves comprises inwardly opening U-shaped flanges along the edges of the unicentric arcuate articular surface of (b) and substantially congruent mating grooves in the unicentric arcuate articular surface of (c).

3. The prosthetic joint of claim 2 wherein the Ushaped flanges of (b) include an open portion on both edges of the arcuate articular surface of (b) which open portion enables the arcuate articular surface of (c) to be mated with the arcuate articular surface of (b) prior to arcuate relative movement therebetween which movement engages the system of interlockable flanged grooves.

* * * * *